United States Patent [19]

Jackson et al.

[11] Patent Number: 5,756,459

[45] Date of Patent: May 26, 1998

[54] INSECTICIDALLY EFFECTIVE PEPTIDES ISOLATABLE FROM PHIDIPPUS SPIDER VENOM

[75] Inventors: John Randolph Hunter Jackson; Eric DelMar; Janice Helen Johnson; Robert Marden Kral, Jr., all of Salt Lake City, Utah

[73] Assignees: FMC Corporation, Philadelphia, Pa.; NPS Pharmaceuticals, Inc., Salt Lake City, Utah

[21] Appl. No.: 484,357

[22] Filed: Jun. 7, 1995

[51] Int. Cl.$^6$ .......................... A61K 38/16; C07K 14/435
[52] U.S. Cl. ...................................... 514/12; 530/350
[58] Field of Search ........................... 514/12; 530/350

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,703,008 | 10/1987 | Lin | 435/240.2 |
| 4,797,279 | 1/1989 | Karamata et al. | 424/93 |
| 4,855,405 | 8/1989 | Yoshioka et al. | 530/300 |
| 4,861,595 | 8/1989 | Barnes et al. | 424/195.1 |
| 4,879,236 | 11/1989 | Smith et al. | 435/235 |
| 4,918,107 | 4/1990 | Nakajima et al. | 514/616 |
| 4,925,664 | 5/1990 | Jackson et al. | 424/537 |

FOREIGN PATENT DOCUMENTS

| | | |
|---|---|---|
| 2005658 | 6/1990 | Canada. |
| 0 325 400 A1 | 7/1989 | European Pat. Off. |
| 0 340 948 | 11/1989 | European Pat. Off. |
| 0 374 940 | 6/1990 | European Pat. Off. |
| 0 395 357 | 10/1990 | European Pat. Off. |
| 0 431 829 | 6/1991 | European Pat. Off. |
| 0 505 207 | 9/1992 | European Pat. Off. |
| WO 89/07608 | 8/1989 | WIPO. |
| WO 92/16637 | 10/1992 | WIPO. |
| WO 93/23428 | 11/1993 | WIPO. |

OTHER PUBLICATIONS

Adams, et al., "Isolation and Biological Activity of Synaptic Toxins from the Venom of The Funnel Web Spider, *Agelenopsis aperta*", in Insect Neurochemistry and Neurophysiology 1986, Borkevec and Gelman, eds., Humana Press, New Jersey, 1986.

Carbonell, et al., "Synthesis of a gene coding for an insect–specific scorpion neurotoxin and attempts to express it using baculovirus vectors", *Gene*, 73:409–418 (1988).

Chomczynski, et al., "Single–Step Method of RNA Isolation by Acid Guanidinium Thiocyanate–Phenol–Chloroform Extraction", *Analytical Biochemistry*, 162:156–159 (1987).

Cutler, et al., "Electroporation: Being Developed to Transform Crops, (success with model crop confirmed)", *AG Biotech. News*, (5):3 & 17 (1990).

Davies, et al., "Recombinant baculovirus vectors expressing gluthathione–S–transferase fusion proteins", *Biotech.*, 11:933–936 (1993).

Dunwiddie, T.V., "The Use of In Vitro Brain Slices in Neuropharmacology", *Electrophysiological Techniques in Pharmacology*, H.M. Geller, 25ed. Alan R. Liss, Inc., New York, pp. 65–90 (1986).

Fuqua, et al., "A simple PCR Method for detection and cloning low abundant transcript", *Biotechniques*, 9:206–211 (1990).

Hink, et al., "Expression of three recombinant proteins using baculovirus vectors in 23 insect cell lines", *Biotechnol. Prog.*, 7:9–14 (1991).

Jackson and Parks, "Spider Toxins: Recent Applications in Neurobiology", Ann Rev Neurosci., 12:405–414 (1989).

Jones, et al., "Molecular Cloning Regulation and Complete Sequence of a Hemocyanin–Related Juvenile Hormone–Suppressible Protein From Insect Hemolymphs", *J. Biol. Chem.*, 265:8596–8602 (1990).

Miller, et al., "Bacterial, Viral and Fungal Insecticides", *Science*, 219:715–721 (1983).

Rossi, et al., "An Alternate Method for Synthesis of Double–Stranded DNA Segments", *J. Biol. Chem.*, 257:9226–9229 (1982).

Saiki, et al., "Primer–Directed Enzymatic Amplification of DNA with a Thermostable DNA Polymerase", *Science*, 239:487–491, 1988.

Scopes, "Measurement of Protein by Spectrophotometry at 205 nm", *Anal. Biochem.*, 59:277–282, 1974.

Skinner, et al., "Purification and characterization of two classes of neurotoxins from the funnel web spider, *Agelenopsis aperta*", *J. Biol. Chem.*, 264:2150–2155 (1989).

Stapleton, et al., "Curtatoxins, neurotoxic insecticidal polypeptides isolated from the funnel web spider *Hololena curta*", *J. Biol. Chem.* 265:2054–2059 (1990).

Stewart, et al., "Construction of an improveded baculovirus insecticide containing an insect–specific toxin gene", *Nature*, 352:85–88 (1991).

Summers and Smith, "A Manual of Methods for Baculovirus Vectors and Insect Cell Culture Procedures", *Texas Agricultural Experiment Bulletin*, No. 1555, 1, 1988.

Tomalski and Miller, "Insect paralysis by baculovirus–mediated expression of a mite neurotoxin gene", *Nature*, 352:82–85 (1991).

(List continued on next page.)

*Primary Examiner*—Robert A. Wax
*Assistant Examiner*—Kawai Lau
*Attorney, Agent, or Firm*—Woodcock Washburn Kurtz Mackiewicz & Norris LLP

[57] ABSTRACT

This invention provides a family of insecticidally effective proteins and particular members of that family which may be isolated from the venom of the spider *Phidippus audax*. DNA encoding such proteins, insecticidal compositions of these proteins or the DNA encoding them, and methods for controlling invertebrate pests. Recombinant expression vectors and host cells and methods for producing insecticidally effective peptides are also provided.

3 Claims, 5 Drawing Sheets

OTHER PUBLICATIONS

Vialard, et al., "Synthesis of the Membrane Fusion and Hemagglutinin Proteins of Measles Virus Using a Novel Baculovirus Vector Containing the β–Galactosidase Gene", *J. Virology*, 64:37–50 (1990).

Waddel and Hill, "A Simple Ultraviolet Spectrophotometric Method for the Determination of Protein", *J. Lab. Clin. Med.* 48:311–314 (1956).

Zlotkin, et al., "An Excitatory and a Depressant Insect Toxin from Scorpion Venom both Affect Sodium Conductance and Possess a Common Binding Site", *Arch. Biochem. and Biophysics*, 240:877–887 (1985).

McCutchen, et al., "Development of a Recombinant Baculovirus Expressing an Insect-Selective Neurotoxin: Potential for Pest Control", *Biotechnology*, 9:848–851, 1991.

Bentzien, "Biology of the Spider *Diguetia imperiosa*", *The Pan–Pacific Entomologist*, 49:110–123, 1973.

Quicke, et al., "Extended summaries Pesticides Group and Physicochemical and Biophysical Panel Symposium Novel Approaches in Agrochemical Research", *Pestic. Sci.*, 20:315–317, 1987.

Quistad, et al., "Insecticidal Activity of Spider (Araneae), Centipede (Chilopoda), Scorpion (Scorpionida), and Snake (Serpentes) Venoms", *J. Econ. Entom.*, 85:33–39.

Nentwig, et al. "Comparative Investigations on the Effect of the Venoms of 18 Spider Species onto the Cockroach *Blatta orientalis*(Blattodea)", *Zool. Jb. Physiol.* 96:279–290 (1992).

Friedel, et al., "Immobilizing and Lethal Effects of Spider Venoms on the Cockroach and the Common Mealbeetle", *Toxicon*, 27:305–316, 1989.

Roth, "The Spider Genus Tegenaria in the Western Hemisphere (Agelenidae)", *Amer. Museum Novitates*, 2323:1–33, 1968.

Vest, "Necrotic Arachnidism in the Northwest United States and Its Probably Relationship to *Tegenaria agrestis* (Walckenaer) Spiders", *Toxicon*, 25:175–184, 1987.

Creighton, "Modification of the Amino and Carboxyl Terminal Groups", *Proteins: Structure and Molecular Properties*, W.H. Freeman and Company: New York, pp. 75–76, 1983.

Blobel, "Intracellular Protein Topogenesis", *Proc. Natl. Acad. Sci. USA*, 77:1496–1500, 1980.

Raineri, et al., "Agrobacterium–Mediated Transformation of Rice (*Oryza sativa L.*)", *Biotechnology*, 8:33–38, 1990.

Fromm, et al., "Inheritance and Expression of Chimeric Genes in the Progeny of Transgenic Maize Plants", *Biotechnology*, 8:833–839, 1990.

Smith et al. "$M_r$ 26,000 antigen of *Schistosoma japonicum* recognized by resistant WEHI 129/J mice is a parasite gluthathione S–transferase", *Proc. Natl. Acad. Sci. USA*, 83:8703–8707, 1986.

Raymond, "Presentation d'un programme Basic d'analyse log–probit pour micro–ordinateur", *Set. Ent. med et Parasitol.*, 23:117–121 1985.

Luria, et al., *In General Virology*, John Wiley and Sons: New York, Chapter 2, pp. 21–32, 1978.

Kuroda, et al., "Synthesis of Biologically Active Influenza Virus Hemagglutinin in Insect Larvae", *J. of Virology*, 63:1677–1685, 1989.

Wood, "Protease Degradation of *Autographa californica* Nuclear Polyhedrosis Virus Proteins", *Virology*, 103:392–399, 1980.

Price, et al., "Complementation of recombinant baculoviruses by coinfection with wild–type facilitates production in insect larvau of antigenic proteins of hepatitis B virus and influenza virus", *Proc. Natl. Acad. Sci. USA*, 86:1453–1456, 1989.

Bers, et al., "Protein and Nucleic Acid Blotting and Immunobiochemical Detection", *BioTechniques*, 3:276–288, 1985.

Bronstein, et al., "Rapid and Sensitive Detection of DNA in Southern with Chemiluminescence", *BioTechniques*, 8:310–314, 1990.

Quistad, et al., "Paralytic and Insecticidal Toxins from the Funnel Web Spider, *Hololena curta*", *Toxicon*, 29:329–336, 1991.

Bowers, et al., "Identification and purification of an irreversible presynaptic neurotoxin from the venom of spider *Hololena curta*", *Proc. Natl. Acad. Sci. USA*, 84:3506–3510, 1987.

Geren, "Neurotoxins and Necrotoxins of Spider Venoms", *J. Toxicol. –Toxin Reviews*, 5:161–170, 1986.

Grishin, "Toxic components from *Buthus eupeus* and *Lycosa singoriensis* venoms", Front. Bioorg. Chem. Mol. Biol., Proc. Int. Symp. (1980). Ed: Ananchenko. Pergamon: Oxford, England, pp. 93–96.

Hermann and Frischauf, "Isolation of Genomic DNA", *Methods in Enzymology*, 152:180–183, 1987.

Kaneda, et al., "Scorpion toxin prolongs an inactivation phase of the voltage dependent sodium current in rat isolated single hippocampal neurons", *Brain Res.*, 487:192–195, 1989.

McKnight, et al., "Transcriptional Control Signals of an Eucaryotic Protein–Coding Gene", *Science*, 217, 316–324, 1982.

Barrett, S.M.et al. (1993) "Passive hemagglutination inhibition test for diagnosis of brown recluse spider bite envenomation" Clin. Chem. 39(10):2104–2107, Oct. 1993.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13 amino acid residues
        ( B ) TYPE: amino acid
        ( D ) TOPOLOGY: unknown     ( x i ) SEQUENCE DESCRIPTION: SEQ ID NO:1:

```
Asp Gly Ile Val Gly Lys Ala Ser Ser Tyr Ala Ala Leu
 1               5                  10
```

INSECTICIDALLY EFFECTIVE PEPTIDES ISOLATABLE FROM PHIDIPPUS SPIDER VENOM

FIELD OF THE INVENTION

This invention relates to insecticidally effective proteins. More particularly, the invention relates, inter alia, to a family of insecticidally effective proteins which may be isolated from Phidippus spider venom as well as methods for controlling invertebrate pests.

BACKGROUND OF THE INVENTION

In recent years, scientists and the general public have become increasingly aware that the use of conventional chemical insecticides may have undesirable environmental consequences. These include groundwater contamination, toxicity to non-target organisms such as birds and fish, and potential human health hazards arising from acute or chronic exposure. However, the need for effective insect control has not diminished. This has prompted researchers to develop novel agents for insect control, including improved microbial insecticides.

The most widely used microbial pesticides are derived from the bacterium *Bacillus thuringiensis* (hereinafter B.t.). This bacterial agent is used to control a variety of pests, including leaf-eating caterpillars, beetles and mosquitos. U.S. Pat. No. 4,797,279 issued Jan. 10, 1989 to Karamata, et al., discloses hybrid bacterial cells comprising the gene coding for *B.t. kurstaki* delta-endotoxin and the gene coding for *B.t. tenebrionis* delta-endotoxin and their preparation. The B.t. hybrids are active against pests susceptible to *B. t. kurstaki* strains as well as against pests susceptible to *B.t. tenebrionis* strains. Generally, these hybrids have useful insecticidal properties which are superior to those observed by physical mixtures of the parent strains in terms of level of insecticidal activity, or in terms of spectrum of activity, or both. The insecticidal compositions comprising such microorganisms may be used to combat insects by applying the hybrids in an insecticidally effective amount to the insects or to their environment.

Another derivation from the bacterium B.t. was disclosed in European Patent Application, Publication No. 0325400A1, issued to Gilroy and Wilcox. This invention relates to a hybrid toxin gene which is toxic to lepidopteran insects. Specifically, the invention comprises a hybrid delta endotoxin gene comprising part of the B.t. var. kurstaki HD-73 toxin gene and part of the toxin gene from B.t. var. *kurstaki* strain HD-1. The hybrid toxin gene (DNA) encoding a protein having activity against lepidopteran insects was disclosed.

The bacterium B.t. was also utilized for its insecticidal properties in European Patent Application, Publication No. 0340948,issued to Wilcox, et al. This invention concerns hybrid pesticidal toxins which are produced by the fusion of an insect gut epithelial cell recognition region of a B.t. gene to diphtheria toxin B chain to prepare a hybrid B.t. toxin which is active against lepidopteran insects. It was suggested that the hybrid B.t. gene may be inserted into a plant or cloned into a baculovirus to produce a toxin which can be recovered. Alternatively, the host containing the hybrid B.t. gene can be used as an insecticide by direct application to the environment of the targeted insect.

In the search for insecticidal compounds, scorpion venom was identified as a possible source of compounds providing insecticidal properties. Two insect selective toxins isolated from the venom of the scorpion *Leirus quinquestriatus quinquestriatus* were revealed in Zlotkin, et al., *Arch Biochem and Biophysics*, 1985, 240, 877–87. In a study related to their chemical and pharmacological properties, it was revealed that one toxin induced fast excitatory contractive paralysis of fly larvae and the other induced slow depressant flaccid paralysis. Both affected sodium conductance in neurons.

Canadian Patent 2,005,658 issued Jun. 19, 1990 to Zlotkin, et al., discloses an insecticidally effective protein derived from the scorpion *Leiurus quinquestriatus hebraeus*. In this invention, the venom is lyophilized and separated into fractions. The fraction with the highest toxicity to blowfly larvae and the lowest toxicity to mice was subjected to further purification and the final product is that referred to as "LqhP35".

Corresponding with the research and developments related to various compositions having insecticidal properties, researchers worked to develop methods for producing insecticidal genes and introducing these to the target to be protected, or into microbial delivery systems. A method for producing insecticidal genes and introducing them to the target to be protected was disclosed in Cutler, *AG Biotech. News*, 1990,vol. 7(5):3 & 17. This article teaches that DNA may be electroporated directly into germinating pollen and that pollen may be put back on the flower to form seeds which then grow into transformed plants. This method has been employed successfully in tobacco plants and may be successful in corn and alfalfa as well. This method may be easier than the electroporation of protoplasts because the ultimate goal is to pollinate the flowers and "let the flowers do the work" rather than to regenerate the plant. The process consists of collecting pollen, germinating it in a germinating medium for 30–60 minutes after which the pollen tube will start to come out of the pollen grain, adding the desired DNA to the liquid suspension containing the pollen, administering an electric shock to open the pores of the pollen, washing the excess DNA away, and putting the altered pollen under the stigma of a plant and waiting until seeds are formed. This may be an easy method to move any gene into crop plants.

An additional delivery system was disclosed in U.S. Pat. No. 4,861,595 issued Aug. 29, 1989 to Barnes and Edwards. This invention concerns the use of treated, substantially intact, microbial cells as a delivery system of protein compounds to animals and humans. The microbial cells initially produce a protein intracellularly via a homologous gene. The protein-producing microbe is treated by chemical or physical means while the cell is substantially intact. Manipulation of the treatment process produces a nonproliferative treated microbial cell without significant loss of the activity of the intracellular compound. Since the cell will not replicate and will have a stable cell wall which may then be broken down in a desired area of the digestive system of the animal or human, it allows the timed or targeted release of the products encapsulatable by the subject invention. After suitable treatment, the protein-producing microbial cell itself is used as the delivery system so no purification of the produced compound is necessary. Any protein, polypeptide, amino acid, or compound, including insecticides, that may be produced by microbial means may be the starting material of the invention.

U.S. Pat. No. 4,879,236 issued Nov. 7, 1989 to Smith and Summers, relates to a method for incorporating a selected gene coupled with a baculovirus promoter into a baculovirus genome to produce a recombinant baculovirus expression vector capable of expression of the selected gene in an insect cell. The method involves cleaving baculovirus DNA to produce a DNA fragment comprising a polyhedrin gene or portion thereof, including a polyhedrin promoter. To prepare a recombinant transfer vector, the DNA fragment is inserted into a cloning vehicle and then a selected gene is inserted into this modified cloning vehicle such that it is under the control of the polyhedrin promoter. The recombinant transfer vector is then contacted in insect cells with a baculovirus DNA so as to effect recombination and incorporation of the selected gene into the baculovirus genome. The baculovirus *Autographa californica* (AcMNPV) and its associated polyhedrin promoter were found to be useful in producing a viral expression vector capable of extremely high levels of expression of a selected gene in an insect host cell.

The inventors suggest that the expression vector might be used in a system for controlling insects by selecting a gene which produces a protein which is toxic to a specific insect or to a spectrum of insects and cloning that gene into the AcMNPV expression vector. They suggest that the vector could be applied to the plant or animal to be protected. The recombinant virus could invade the cells of the intestinal wall following ingestion by the insect and begin replication.

The possibility of using DNA technology to incorporate a synthetic gene which encodes a neurotoxin found in scorpion venom was explored in Carbonell, et al., *Gene*, 1988, 73, 409–18. This article describes the possibility of using DNA technology to incorporate a synthetic gene which encodes a neurotoxin found in the venom of the scorpion, *Buthus eupeus*, into the baculovirus genome to improve baculovirus pesticides. Three methods of expression using the polyhedrin promoter-based AcMNPV expression system to effect toxin production were studied. Expression of the 36 codon gene alone provided minuscule production of the toxin. Some success was found with the attachment of a signal peptide to the toxin. Significant levels of protein were produced when the toxin gene was fused to the N-terminus of polyhedrin. However, production was ten to twenty-fold less than that observed for polyhedrin itself. The limitation to expression was not believed to be at the level of transcription but at the post-transcriptional level including translation and protein stability. Paralytic activity of the toxin products was not detected. However, Carbonell's failure to express a synthetic gene encoding a specific neurotoxin in a baculovirus vector is not predictive of the state of the art. To the contrary, several publications indicate the opposite.

Davies, et al., *Biotech.*, 1993, 11, 933–36,in describing a method for recombinant protein expression using baculovirus vectors, noted that the baculovirus system may be used to express almost any heterologous gene of interest, including functional recombinant proteins. Other publications describing a method for recombinant protein expression using baculovirus vectors include Tomalski, et al., *Nature*, 1991, 352, 82–85;Stewart, et al., *Nature*, 1991, 352, 85–88;and McCutchen, et al., *Biotechnology*, 1991, 9, 848–851.

Researchers have also been able to isolate toxins extracted from the venom of spiders. U.S. Pat. No. 4,925,664 issued to Jackson and Parks on May 15, 1990, discloses methods of treating heart and neurological diseases by applying toxins derived from the spiders *Agelenopsis aperta* and *Hololena curta*. The toxins are also effective as specific calcium channel or excitatory amino acid receptor blockers that may be used against insects and related pests.

Another study related to the properties of isolated spider venom toxins revealed the ability of low molecular weight factors isolated from funnel-web spider venoms to reversibly bind to calcium channels. WO 89/07608 issued Aug. 24, 1989 to Cherksey, et al., discloses that these active low molecular weight factors reversibly bind to calcium channels with sufficient specificity and affinity to extinguish calcium conductance in neurons and to permit isolation and purification of calcium channel structures. These venoms were found to be toxic to mammals.

Other applications of spider toxins were discussed in Jackson and Parks, *Ann. Rev. Neurosci.*, 1989, 12, 405–14. This article describes the great heterogeneity in the toxins of different taxa. It recognizes that experiments have suggested species-specific properties of calcium channels and the spider venoms might provide calcium channel antagonists. The spider venoms discussed are found to affect vertebrates. The article also identifies spider venoms as possible sources of insect-specific toxins for agricultural applications.

Adams, et al., "Isolation and Biological Activity of Synaptic Toxins from the Venom of the Funnel Web Spider. *Agelenopsis aperta*," in Insect Neurochemistry and Neurophysiology 1986,Borkovec and Gelman (Eds.), Humana Press, New Jersey, 1986,teaches that multiple peptide toxins which antagonize synaptic transmission in insects have been isolated from the spider *Agelenopsis aperta*.

U.S. Pat. No. 4,855,405 issued Aug. 8, 1989 to Yoshioka, et al., discloses a receptor inhibitor obtained from Joro spider (*Nephila clavata*) venom, and its manufacturing method. Yoshioka demonstrates that their toxins show glutamate receptor inhibitory activity in an insect electrophysiological assay.

U.S. Pat. No. 4,918,107 issued Apr. 17, 1990 to Nakajima, et al., relates to a compound which has glutamate receptor inhibitor activity, a process for preparing the same, and an insecticidal composition containing the same.

Accordingly, due to a combination of problems associated with conventional chemical insecticides, including pest resistance and injurious effects on non-target organisms, there exists a continuing need for the development of novel means of invertebrate pest control.

SUMMARY OF THE INVENTION

There are provided by this invention novel insecticidally effective proteins derived from, for example, a spider of the genus Phidippus. Two proteins, exhibiting insecticidal activity, were isolated from the chromatographical separation of Phidippus whole venom toxin. The proteins are designated BW2 and BW5.

Further provided by this invention are methods for controlling invertebrate pests with insecticidal compositions containing insecticidal proteins or the genes encoding these proteins and insecticidal compositions.

Still further provided by this invention are novel recombinant expression vectors and genetically engineered insecticidal microbes and methods of controlling invertebrate pests comprising contacting said pests with a recombinant baculovirus capable of expressing an effective amount of an insecticidally effective peptide substantially isolatable from Phidippus spider venom and agriculturally or horticulturally acceptable salts thereof.

DETAILED DESCRIPTION OF THE DRAWINGS

DETAILED DESCRIPTION OF THE INVENTION

*Phidippus audax* is a member of the Family Salticidae, better known as the jumping spiders. It is widely distributed in the United States, and is especially common in the southern states. *P. audax* is one of the larger members of the family, sometimes exceeding half an inch in length. *P. audax*, like most other salticids, is a hunting spider, relying on agility and visual acuity to detect and capture prey.

The mechanism of action of the insecticidally effective proteins of this invention is unknown. It has been found that these toxins produce a characteristic set of symptoms in lepidopteran larvae. These include a rapidly developing flaccid paralysis, complete cessation of dorsal vessel contractions (heartbeats), and in some cases a gradually spreading zone of necrotic or cyanotic discoloration. Paralysis generally develops in less than ten minutes, and was observed in some cases to develop in less than two minutes. These effects are identical to those caused by whole Phidippus venom, strongly implying that the toxic proteins described in this invention are primarily responsible for the insecticidal effects of this venom.

A. The Isolation of Proteins from Phidippus Venom

One source of insecticidally effective proteins is Phidippus venom. Spider venom can be removed from Phidippus by any method known such as venom gland extraction from cephalothorax. However, in order to avoid impurities within the spider venom and the isolated toxins, the spider venom preferably is obtained by electrical stimulation of the spiders to cause release of the venom and subsequent suction to collect the released venom and prevent contamination of the venom by regurgitate or hemolymph as described in U.S. Pat. No. 4,925,664.

Once the spider venom is obtained by electrical milking techniques, it can be fractionated into its protein (toxin) components by high performance liquid chromatography (HPLC) with a variety of separation modes such as ion exchange and immobilized metal ion affinity chromatography (IMAC), and chromatofucusing.

Thus, using the technique of electrically milking the spider coupled with HPLC using IMAC, ion exchange and chromatofocusing columns, it is possible to obtain substantially purified spider toxins. It will be appreciated, however, that other equivalent techniques may also be employed within the scope of the present invention in order to isolate the spider toxins. The toxins thus isolated can be assayed for insecticidal activity and the DNA and amino acid sequences determined by methods known to those in the art.

B. Insecticidally Effective Proteins

This invention, in one of its aspects, provides a family of insecticidally effective proteins, and insecticidally effective fragments thereof and agriculturally or horticulturally acceptable salts thereof.

Once an insecticidally effective, protein-containing fraction has been isolated from a source and purified as described herein, amino acid sequence determination can be performed in any way known to those in the art such as N-terminal amino acid sequencing and use of an automated amino acid sequencer. The entire amino acid sequence can be determined.

It will be understood from this disclosure that additional insecticidally effective proteins are expected to be within the scope of the invention. That is, it is believed other insecticidally effective proteins in the family exist and may be isolatable from Phidippus as well as other sources in addition to the two detailed herein.

C. Identification of the Coding Sequence of Insecticidally Effective Proteins of this Invention A substantially isolated DNA sequence encoding a protein of this invention may be determined by methods known to those in the art.

Employing partial amino acid sequence data, the genes responsible for the production of proteins from a source can be isolated and identified. Numerous methods are available to obtain the gene responsible for the production of a protein. Examples include Fuqua, et al., *Biotechnique*, Vol. 9,No. 2 (Aug 1990); Frohman, "RACE: Rapid amplification of cDNA ends", in PCR protocols, Innis, et al. (Eds.), Academic Press, San Diego, Calif., (1990) and U.S. Pat. No. 4,703,008,which patent is incorporated herein by reference.

Briefly, a "degenerate" series of DNA oligonucleotides are synthesized which encode the determined amino acid sequence or which represents the complementary DNA (cDNA) strand to such a DNA molecule which encodes the determined amino acid sequence. These synthetic DNA oligonucleotides may then be used to probe for DNA sequence homology in cell clones containing recombinant DNA molecules comprising, in part, DNA sequences derived from the genomic DNA of an organism such as a spider or derived from cDNA copies of mRNA molecules isolated from cells or tissues of an organism such as a spider. Generally, DNA molecules of fifteen (15) nucleotides or more are required for unique identification of an homologous DNA, said number requiring unique determination of at least five (5) amino acids in sequence. It will be appreciated that the number of different DNA oligonucleotides which can encode the determined amino acid sequence may be very large since each amino acid may be encoded by up to six (6) unique trinucleotide DNA sequences or codons. Therefore, it is impractical to test all possible synthetic DNA probes individually, and pools of several such DNA oligonucleotides are used concomitantly as probes. The production of such pools which are referred to as "degenerate" probes is well known in the art. It will also be appreciated that while only one DNA oligonucleotide in the probe mixture will have an exact sequence homology to the gene of interest, several of the synthetic DNA oligonucleotides in the pool may be capable of uniquely identifying said gene since only a high degree of homology is required. Therefore, successful isolation of the gene of interest may be accomplished with synthetic DNA oligonucleotide probe pools which do not contain all possible DNA sequences. In general, codons which are infrequently utilized by the organism need not be represented in the oligonucleotide probe pool. In fact, a single sequence DNA probe may be produced by including only the DNA codons most frequently utilized by the organism for each amino acid, although, it will be appreciated that this approach is not always successful.

One technique to isolate a gene sequence employs the Polymerase Chain Reaction (PCR) . See e.g., U.S. Pat. Nos. 4,683,195 and 4,683,202 which patents are incorporated by reference as if fully set forth herein. Essentially, PCR allows the amplification of a selected DNA sequence when at least one of the two terminal portions of the sequence are known. Primers, or oligonucleotide probes, are designed which correspond to the 5' ends of both complimentary strands of the sequence of interest. Using PCR with the addition of deoxynucleotide bases and a heat stable polymerase, the portion of the DNA sequence between the primers is then synthetically constructed. Numerous cycles of PCR thus allow a logarithmic amplification of even a single copy of a DNA sequence.

In one such method of employing PCR to obtain the gene which encodes a unique spider venom toxin, RNA is isolated from the spider and purified by methods known in the art. Reverse transcriptase and random primers are then used to reverse transcribe the spider RNA into cDNA. Alternatively, oligo(dT) can be used, instead of random primers, to specifically reverse transcribe mRNA. The "degenerate" mixture of synthetic DNA oligonucleotides encoding the 5'-termini of the cDNA, corresponding to the amino-terminus of the protein, and the 5'-termini of its complimentary strand, corresponding to the carboxy-terminus of the protein, is then designed with a restriction endonuclease site on their 5'-termini. This restriction site allows for the insertion of the cloned DNA fragment into a cloning vector. This DNA oligonucleotide mixture is used to prime a PCR reaction. Because the synthetic DNA oligonucleotide mixture used to prime the PCR reaction is specific to the desired sequence, only the desired cDNA will be effectively amplified. The resultant product represents an amplified cDNA which can be ligated to any of a number of known cloning vectors. Not withstanding this, it will be appreciated that "families" of proteins or peptides may exist in spider venoms which will have similar amino acid sequences and that in such cases, the use of mixed oligonucleotide primer sequences may result in the amplification of one or more of the related cDNAs encoding these related proteins. Genes encoding related proteins are also within the scope of the invention as the related proteins also have useful insecticidal activities.

Finally, the produced cDNA sequence can be cloned into an appropriate vector using conventional techniques, analyzed and the nucleotide base sequence determined. A direct amino acid translation of these PCR products will reveal that they corresponded to the complete coding sequence for the mature protein. The portion of the DNA sequence which might encode amino acids corresponding to precursor and or propeptide regions may not be obtained by this approach. Such sequences may be determined by isolation of genomic or cDNA clones using the cDNA clone produced in this approach as a hybridization probe which is within the scope of the art.

D. Application of the Proteins as Insecticides

The insecticidally effective proteins of this invention are believed to be useful in controlling invertebrate pests such as those in the order Lepidoptera. Methods for using the insecticidally effective proteins of this invention may include contacting the pests with an effective amount of a protein of this invention.

Methods of contacting an invertebrate pest with a protein to control said pests are known. Examples include the insertion of a gene encoding a toxic peptide or protein into the genome of a baculovirus, such as the *Autographa californica* nuclear polyhedrosis virus. Of course, methods of controlling invertebrate pests using the proteins of this invention can be used in combination with other methods of controlling pests.

E. Recombinant expression

As used herein, "expression vector" includes vectors which are capable of expressing the desired peptide or protein from DNA sequences contained therein, where such sequences are operably linked to other sequences capable of effecting their expression, i.e., promoter sequences. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of supporting expression of a specified DNA code disposed therein is included in this term as it is applied to the specified sequence. In general, expression vectors of utility in recombinant DNA techniques are often in the form of "plasmids" which refer to circular double stranded DNA which, in their vector form are not bound to the chromosome. "Plasmid" and "vector" are used interchangeably as the plasmid is the most commonly used form of vector. However, the invention is intended to include such other forms of expression vectors which serve equivalent functions and which become known in the art subsequently hereto.

"Recombinant host cells" refers to cells which have been transformed with vectors constructed using recombinant DNA techniques.

Further provided by this invention is a recombinant expression vector comprising a DNA sequence which encodes an insecticidally effective peptide substantially isolatable from Phidippus spider venom. The vector is capable of effecting the expression of the coding sequence in transformed cells. Also provided by the invention are recombinant host cells with a DNA sequence encoding an insecticidally effective peptide substantially isolatable from Phidippus spider venom in a manner allowing the host cell to express the peptide.

Such recombinant expression vectors may be employed in methods for producing insecticidally effective peptides. Such methods comprise culturing recombinant host cells wherein a recombinant expression vector transformed, transfected or otherwise applied in said host cells has a DNA sequence encoding the peptide and recovering the insecticidally effective peptide from the recombinant host cell culture or host organism. In such methods the vector is capable of supporting with host cell factors the expression of the coding sequence in the transformed cells.

Provision of a suitable DNA sequence encoding the desired protein permits the production of the protein using recombinant techniques now known in the art. The coding sequence can be obtained by retrieving a cDNA or genomic sequence from a native source of the protein or can be prepared synthetically using the accurate amino acid sequence determined from the nucleotide sequence of the gene. When the coding DNA is prepared synthetically, advantage can be taken of known codon preferences of the intended host.

Expression systems containing the requisite control sequences, such as promoters, and preferably enhancers and termination controls, are readily available and known in the art for a variety of hosts. See e.g., Sambrook, et al., *Molecular Cloning a Laboratory Manual*, Second Ed., Cold Spring Harbor Press, New York (1989).

Thus, the desired proteins can be prepared in both procaryotic and eucaryotic systems, resulting, in the case of many proteins, in a spectrum of processed forms.

The most commonly used procaryotic system remains *E. coli*, although other systems such as *B. subtilis* and Pseudomonas are also expected to be useful. Suitable control sequences for procaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in procaryotic hosts in this matter, the signal sequence is removed upon secretion.

A wide variety of eucaryotic hosts are also now available for production of recombinant foreign proteins. As in bacteria, eucaryotic hosts may be transformed with expression systems which produce the desired protein directly, but more commonly signal sequences are provided to effect the secretion of the protein. Eucaryotic systems have the additional advantage that they are able to splice introns which may occur in the messenger RNA encoding proteins of higher organisms. Eucaryotic systems also provide a variety of post-translational mechanisms which result in, for example, glycosylation, oxidation or derivatization of certain amino acid residues, conformational control, and so forth.

Commonly used eucaryotic systems include yeast, insect cells, mammalian cells, avian cells, and cells of higher plants. The list is not exhaustive. Suitable promoters are available which are compatible and operable for use in each of these host types as well as are termination sequences and enhancers, as e.g. the baculovirus polyhedrin promoter. As above, promoters can be either constitutive or inducible. For example, in mammalian systems, the MTII promoter can be induced by the addition of heavy metal ions.

The particulars for the construction of expression systems suitable for desired hosts are known to those in the art. For recombinant production of the protein, the DNA encoding it is suitably ligated into the expression system of choice, and the system is then transformed into the compatible host which is then cultured and maintained under conditions wherein expression of the foreign gene takes place. The insecticidally effective protein of this invention thus produced is recovered from the culture, either by lysing the cells or from the culture medium as appropriate and known to those in the art.

It is understood that minor modifications of primary amino acid sequence may result in proteins which have substantially equivalent or enhanced activity as compared to the peptides exemplified herein. These modifications may be deliberate, as through site directed mutagenesis, or may be accidental such as through mutations in hosts which produce the peptide of the invention, all these modifications are included so long as insecticidal activity is retained. A "mutation" in a protein alters its primary structure (relative to the commonly occurring or specifically described protein) due to changes in the nucleotide sequence of the DNA which encodes it. These mutations specifically include allelic variants. Mutational changes in the primary structure of a protein result from deletions, additions, or substitutions. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar and/or aromatic. It is generally preferred that encoded peptides differing from the native form contain substituted codons for amino acids which are from the same group as that of the amino acid replaced.

Thus, in general, the basic amino acids Lys, Arg, and His are interchangeable; the acidic amino acids Asp and Glu are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable.

While Pro is a nonpolar neutral amino acid, it represents difficulties because of its effects on conformation, and substitutions by or for Pro are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by codons for amino acids from different classes may also be useful.

Because recombinant materials for the proteins of the invention are provided, these proteins can be made by recombinant techniques as well as by automated amino acid synthesizers. Because of the variety of post-translational characteristics conferred by various host cells, various modifications for the naturally-occurring proteins will also be obtained. A "modified" protein differs from the unmodified protein as a result of post-translational events which change the glycosylation, amidation or lipidation pattern, or the primary, secondary, or tertiary structure of the protein and are of course included within the scope of the invention as claimed.

It should be further noted that if the proteins herein are made synthetically, substitution by amino acids which are not encoded by the gene may also be made. Alternative residues include, for example, the ω amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

F. Genetically Engineered Insecticidal Microbes

The insecticidally effective peptide alone or in combination with another insect toxin is expected to be useful in potentiating or enhancing the toxicity of microbes such as baculoviruses and hybrid bacteria.

Several baculoviruses including those that infect *Heliothis virescens* (cotton bollworm), *Orgyia pseudotsugata* (Douglas fir tussock moth), *Lymantia dispar* (gypsy moth), *Autographa californica* (alfalfa looper), *Neodiprion sertifer* (European pine fly), and *Lanspcyresia pomonella* (codling moth) have been registered in some countries and used as pesticides. Introduction of at least one insect-selective toxin into the genome is expected to significantly enhance the potency of such pesticides.

A recombinant expression vector expected to be particularly suitable for use in this invention is a baculovirus expression vector such as the type disclosed in U.S. Pat. No. 4,879,236,which patent is incorporated by reference as if fully set forth herein. Other publications describing a method for recombinant protein expression using baculovirus vectors include Tomalski, et al., *Nature*, 1991, 352, 82–85;Stewart, et al., *Nature*, 1991, 352, 85–88; and McCutchen, et al., *Biotechnology*, 1991, 9, 848–851. The vector is expected to be useful in a system where a DNA sequence encoding an insecticidally effective peptide substantially isolatable from Phidippus spider venom can be cloned into baculovirus such as *Autographa californica* (AcMNPV) expression vector as described in U.S. Pat. No. 4,879,236 and Miller, et al., *Science*, 1983, 219, 715–721. The recombinant expression vector virus could then be applied to the plant or animal upon which the insect is a pest, and when the virus is ingested by the pest insect, the recombinant virus will invade the cells of the intestinal wall and begin replication. During replication, the gene for the insecticidally effective protein will be expressed, resulting in the disablement or death of the insect in a shorter period than if the insect had ingested the wild type AcMNPV virus.

A hybrid virus also expected to be useful is taught in European Patent Application 0340948. The hybrid virus expressing the DNA of this invention is expected to yield a virus having an altered insect host range. For example, fusion proteins could be expressed as a single polypeptide product of a hybrid gene consisting of DNA of this invention and a specific insect gut cell recognition protein to direct the expressed insecticidally effective peptide to the host insect target.

Various prokaryotic and eucaryotic microbes can be transformed to express a hybrid toxin gene encoding an insecticidally effective protein by the method taught in European Patent Application 0325400.

Hybrid bacterial cells, comprising a plasmid with the gene coding for the protein of this invention are expected to be useful in the method of this invention. Insects would be controlled by applying the hybrids to insects. See e.g., U.S. Pat. No. 4,797,279 which patent is incorporated by reference as if fully set forth herein.

Other examples of employing baculovirus that would be suitable for use in this invention are described in Tomalski, et al., *Nature*, 1991, 352, 82–85 and Stewart, et al., *Nature*, 1991, 352, 85–88); and McCutchen, et al., *Biotechnology*, 1991, 9, 848–851.

An insecticidal composition comprising an insecticidally effective amount of a protein according to this invention and agriculturally or horticulturally acceptable salts thereof in an agriculturally or horticulturally acceptable carrier therefor is also provided.

EXAMPLES

The following examples are given to illustrate particular compositions and methods within the scope of the present invention but they are not intended to limit the scope of the present invention.

MATERIALS AND METHODS
General Separation Methods

The spider venom is preferably obtained by electrical stimulation of the spiders to cause release of the venom and subsequent suction to collect the released venom and prevent contamination of the venom by regurgitate or hemolymph as described in U.S. Pat. No. 4,925,664.

Crude venom (stored at −80° C.) was thawed and mixed thoroughly with the starting solvent prior to chromatography. The venom was fractionated by high performance liquid chromatography (HPLC) incorporating Beckman System Gold 126 solvent delivery and 168 photodiode array detector modules. Several columns and conditions were used in the purifications described below.

Ultrafiltration of the Phidippus crude venom in CENTRICON™ C-3,C-10,and C-100 microconcentrators (Amicon) indicated that the insecticidal activity remained in the retentate. Therefore, HPLC column fractions were generally concentrated in CENTRICON™ C-10 or C-3 microconcentrators for assay in TBW larvae as follows. Column fractions were placed in C-3 filters and centrifuged at approximately 4000×g for 70 min (this concentrated the samples to approximately 200 µl). Two ml of phosphate buffered saline, pH 6.5 (PBS; 136.7 mM NaCl, 2.6 mM KCl, 1.46 mM $KH_2PO_4$, 8.0 mM $Na_2HPO_4$) was added to the concentrate and samples again centrifuged to give a final volume of 150–200 µl.

Immobilized metal ion affinity chromatography (IMAC) was performed on a Progel™ TSK Chelate 5PW column (7.5×75 mm, from Supelco) freshly loaded with $Cu^{+2}$ ions (40 mM $CuSO_4$ (aq)). The A buffer was 20 mM $NaH_2PO_4$, 1 mM imidazole, 0.5M NaCl adjusted to pH 7.0 with 10M NaOH. The B buffer was 20 mM $NaH_2PO_4$, 20 mM imidazole, 0.5M NaCl adjusted to pH 7.0 with 10M NaOH. The column was equilibrated in the A buffer and eluted at 1 ml/min with a 40 min linear gradient from 0% B to 100% B after 5 min at 0% B. After 5 min at 100% B the column was returned to 0% B over 2 min and equilibrated with A buffer before the next injection was made. The effluent was monitored at 280 nm and fractions collected with a Gilson model 203 fraction collector.

Anion exchange chromatography (AEC) was performed on a Mono-Q column (5.0×50 mm). The A buffer was 25 mM Tris base adjusted to pH 7.5 with 6N HCl and the B buffer was 25 mM Tris base, 1.0M NaCl adjusted to pH 7.5 with 6N HCl. The column was eluted at a flow rate of 1 ml/min with a linear gradient (begun 5 minutes after injection) from 0 to 100% B buffer over 75 min. The column was taken to 50% B buffer over 2 min, held at 50% B buffer for 4 min, returned to 0% B buffer over 2 min and equilibrated before the next injection. Chromatography was monitored at 280 nm and fractions collected with a Gilson model 203 fraction collector.

Chromatofocusing was performed using a Mono-P column (5.0×50 mm). Buffer A was 25 mM Bis-Tris adjusted to pH 7.2 and buffer B was Polybuffer 74 diluted 1:10 and adjusted to pH 5.0 with 6N HCl. The column was eluted at a flow rate of 0.5 ml/min with Ok B buffer for 5 min then immediately switched to 100% B buffer. This chromatography was monitored at 280 nm and fractions collected with a Gilson model 203 fraction collector.

Protein concentrations were determined using the Pierce BCA assay reagents and methods unless otherwise noted. N-terminal amino acid sequence analysis was performed at the Biotechnology Center at Utah State University in Logan, Utah.

Insecticidal Activity Methods

The insects tested were last instar, laboratory reared larvae of the tobacco budworm (TBW), *Heliothis virescens*, the cabbage looper (CL), *Trichoplusia ni*, and the beet armyworm (BAW), *Spodoptera exigua*. All samples, whether whole venom or venom fractions, were prepared in filter-sterilized physiological saline (PBS), pH 6.5. Samples were administered by injection into the hemocoel at or near the lateral midline of the fourth abdominal segment; the needle was inserted at a shallow angle to avoid injury to internal organs. After treatment the larvae were held in individual Petri dishes with food and observed periodically for paralysis and other effects such as feeding inhibition. Whole venom doses were calculated in terms of whole venom equivalents (WVE). One WVE is the amount of any material which is normally present in one microliter of whole milked venom. Doses of components from early fractionations were also calculated in terms of WVE. Doses of purified toxins were calculated by protein assay, or by measuring short wavelength ultraviolet absorbances (Scopes, Anal. Biochem., 1974, 59, 277;and Waddell, J. Lab. Clin. Med., 1956, 48, 311). Both methods gave similar results, with calculated concentrations varying by a factor of less than 2.

Example 1

*Phidippus audax* Whole Venom Contains Paralytic Activity

Whole venom was diluted 1:10 or 1:100 in sterile-filtered phosphate-buffered saline (PBS), pH 6.5. Three microliter aliquots of these venom solutions (providing doses of 0.3 or 0.03 WVE/larva) were injected into TBW, BAW, and CL larvae as described previously. The larvae were analyzed initially and after 24 hours for paralysis and the results are indicated in Table I. As indicated in Table I, whole venom contained paralytic activity for all three species tested. Control larvae, which were injected with PBS alone, were unaffected.

TABLE I

*Phidippus audax* Whole Venom Contains Paralytic Activity

| Species | Dose (WVE/larva) | 24 hours[a] | 48 hours[a] |
|---|---|---|---|
| TBW | 0.3 | 5/5 | 5/5 |
| TBW | 0.03 | 4/5 | 4/5 |
| TBW | Control | 0/5 | 0/5 |
| BAW | 0.3 | 6/6 | 6/6 |
| BAW | 0.03 | 6/6 | 6/6 |
| BAW | Control | 0/6 | 0/6 |
| CL | 0.03 | 5/6 | 5/6 |
| CL | Control | 0/6 | 0/6 |

[a]This value represents the number of larvae paralyzed versus total number of larvae injected.

Example 2

Initial Fractionation of *Phidippus audax* Whole Venom by Ultrafiltration and Identification of Paralytic Fractions.

Whole venom was filtered using CENTRICON™ C-3 and C-100 microconcentrators, as described previously, and fractions consisting of the retentates and filtrates were obtained. Various amounts of these fractions were injected into TBW larvae as described previously. The larvae were analyzed initially and after 24 hours for paralysis and the results are indicated in Table II. As indicated in Table II, the paralytic activity was retained in the retentate fractions of both C-3 and C-100 microfiltrations. The specific activity of the C-100 retentate was higher than that of the C-3 retentate, suggesting that the bulk of the activity resides in the C-100 retentate fraction.

TABLE II

Ultrafiltration Fractions of *Phidippus audax* Whole Venom Contains Paralytic Activity in TBW Larvae

| Sample | Dose[a] | Initial[b] | 24 hours[b] |
|---|---|---|---|
| Control (PBS) | — | 0/5 | 0/5 |
| C-3 retentate | 23.5 | 4/5 | 4/5 |
| C-3 filtrate | 24.7 | 0/5 | 0/5 |
| C-100 retentate | 10.0 | 5/5 | 5/5 |
| C-100 filtrate | 16.2 | 0/5 | 0/5 |

[a]This value represents the dosage of the fraction injected in terms of μg of protein per g of larvae.
[b]This value represents the number of larvae paralyzed versus total number of larvae injected.

Example 3

Fractionation of C-100 Retentate of *Phidippus audax* Whole Venom by Immobilized Metal Ion Affinity Chromatography and Identification of Paralytic Fractions.

The C-100 retentate of whole venom was separated by IMAC using a TSK Chelate 5 PW column (7.5×75 mm) loaded with $Cu^{+2}$. The column was eluted at 1 ml/min with a 40 min linear gradient from 0% B to 100% B after 5 min at 0% B. Buffer A was 20 mM $NaH_2PO_4$, 0.5M NaCl, 1 mM imidazole adjusted to pH 7.0. Buffer B was 20 mM $NaH_2PO_4$, 0.5M NaCl, 20 mM imidazole adjusted to pH 7.0. The column was monitored at 280 nm and fractions collected with a Gilson model 203 fraction collector. This separation, depicted in the chromatogram shown in FIG. 1, resulted in the collection of eight fractions. These fractions were injected into TBW larvae as described previously. The larvae were analyzed after 24 and 48 hours and examined for paralysis and feeding inhibition and the results are indicated in Table III. As indicated in Table III, fractions 2, 5, 6 and 8 contained paralytic activity for TBW.

TABLE III

IMAC Fractions of C-100 Retentate of *Phidippus audax* Whole Venom Contains Paralytic and Feeding Inhibitory Activity in TBW Larvae

| Sample | Dose[a] | 24 hours[b] | 48 hours[b] |
|---|---|---|---|
| Control (PBS) | — | 0/3 | 0/3 |
| Cu1 | 21.5 | 0/3 | 0/3 |
| Cu2 | 20.4 | 1/3 | 0/3 |
| Cu3 | 21.6 | 0/3 | 0/3[c] |
| Cu4 | 20.8 | 0/3 | 0/3 |
| Cu5 | 20.0 | 2/3 | 2/3 |
| Cu6 | 21.4 | 3/3 | 1/3[c] |
| Cu7 | 19.7 | 0/3 | 0/3[c] |
| Cu8 | 22.7 | 3/3 | 2/3 |

[a]This value represents the dosage of the fraction injected in terms of μg of protein per g of larvae.
[b]This value represents the number of larvae paralyzed versus total number of larvae injected.
[c]Some of the larvae that were not paralyzed exhibited feeding inhibition at 48 hours.

Example 4

Fractionation of C-100 Retentate of *Phidippus audax* Whole Venom by Immobilized Metal Ion Affinity Chromatography Followed by Anion Exchange Chromatography and Identification of Paralytic Fractions.

Figure 1:
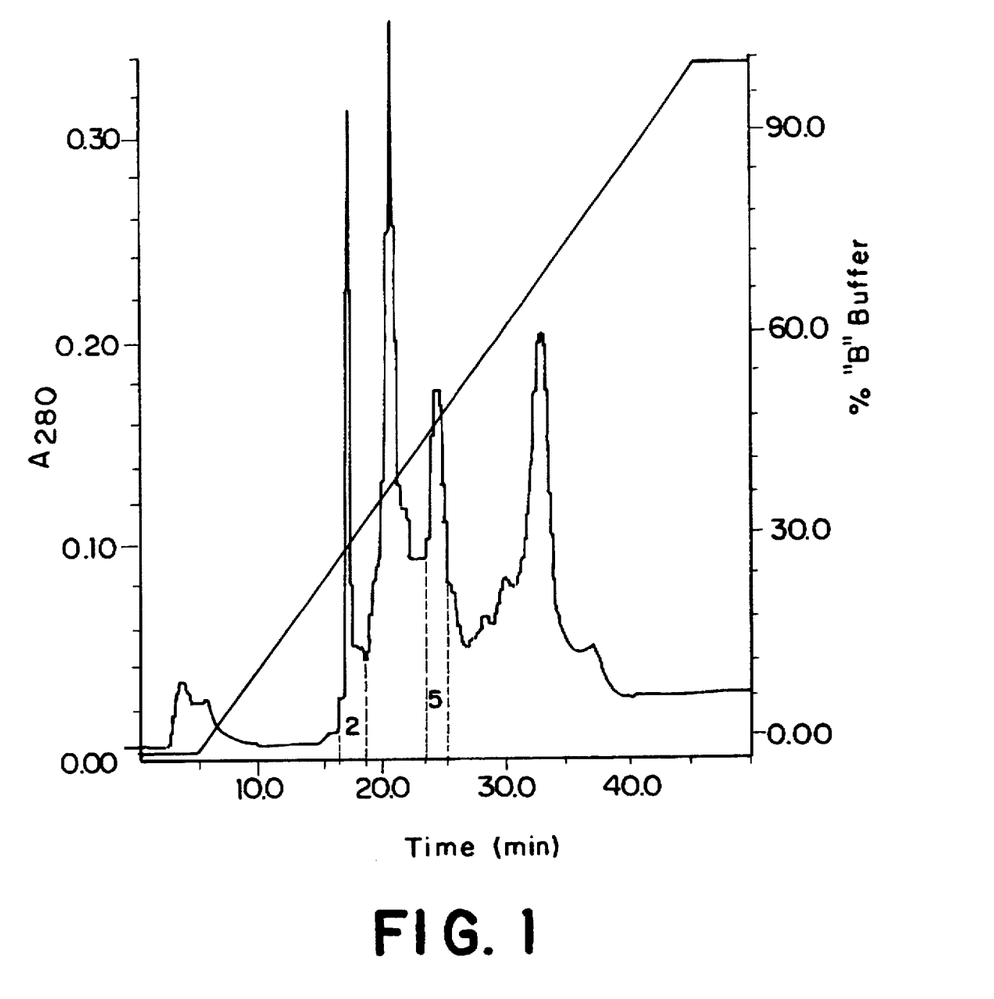
FIG. 1 depicts a chromatogram representing the separation of the C-100 retentate of *Phidippus audax* whole venom by immobilized metal ion chromatography (IMAC) on a TSK Chelate 5 PW column loaded with $Cu^{++}$.

AEC was performed on fractions 2 and 5,depicted in FIG. 1, from the IMAC preparation of C-100 retentate of whole venom using a Mono-Q column (5.0×50 mm). The A buffer was 25 mM Tris base adjusted to pH 7.5 and the B buffer was 25 mM Tris base, 1.0M NaCl adjusted to pH 7.5. The column was eluted at a flow rate of 1 ml/min with a linear gradient from 0 to 100% B buffer over 75 min after 5 min at 0% B. This chromatography was monitored at 280 nm and fractions collected with a Gilson model 203 fraction collector. The anion exchange chromatography of IMAC fractions 2 and 5 of C-100 retentate from whole venom, depicted in the chromatograms shown in FIGS. 2 and 3 respectively, resulted in the collection of three fractions each. Fraction 2 collected from the anion exchange chromatography of IMAC fraction 2 was injected into TBW larvae as described previously. The larvae were analyzed after 1 hour and 48 hours for paralysis and feeding inhibition and the results are indicated in Table IV. As indicated in Table IV, fraction 2 contained paralytic as well as feeding inhibitory activity for TBW.

TABLE IV

AEC Fraction of IMAC Fractions of C-100 Retentate of *Phidippus audax* Whole Venom Contains Paralytic and Feeding Inhibitory Activity in TBW Larvae

| Sample | Dose[a] | 1 hour[b] | 48 hours[b] |
|---|---|---|---|
| Control (PBS) | — | 0/3 | 0/3 |
| #2[c] | 15.5 | 1/3 | 2/3 |

[a]This value represents the dosage of the fraction injected in terms of μg of protein per g of larvae.
[b]This value represents the number of larvae paralyzed versus total number of larvae injected.
[c]All larvae exhibited complete feeding inhibition at 24 hours.

Example 5

Fractionation of C-100 Retentate of *Phidippus audax* Whole Venom by Immobilized Metal Ion Affinity Chromatography Followed by Anion Exchange Chromatography Followed by Chromatofocusing and Identification of Paralytic Fractions.

Figure 2:
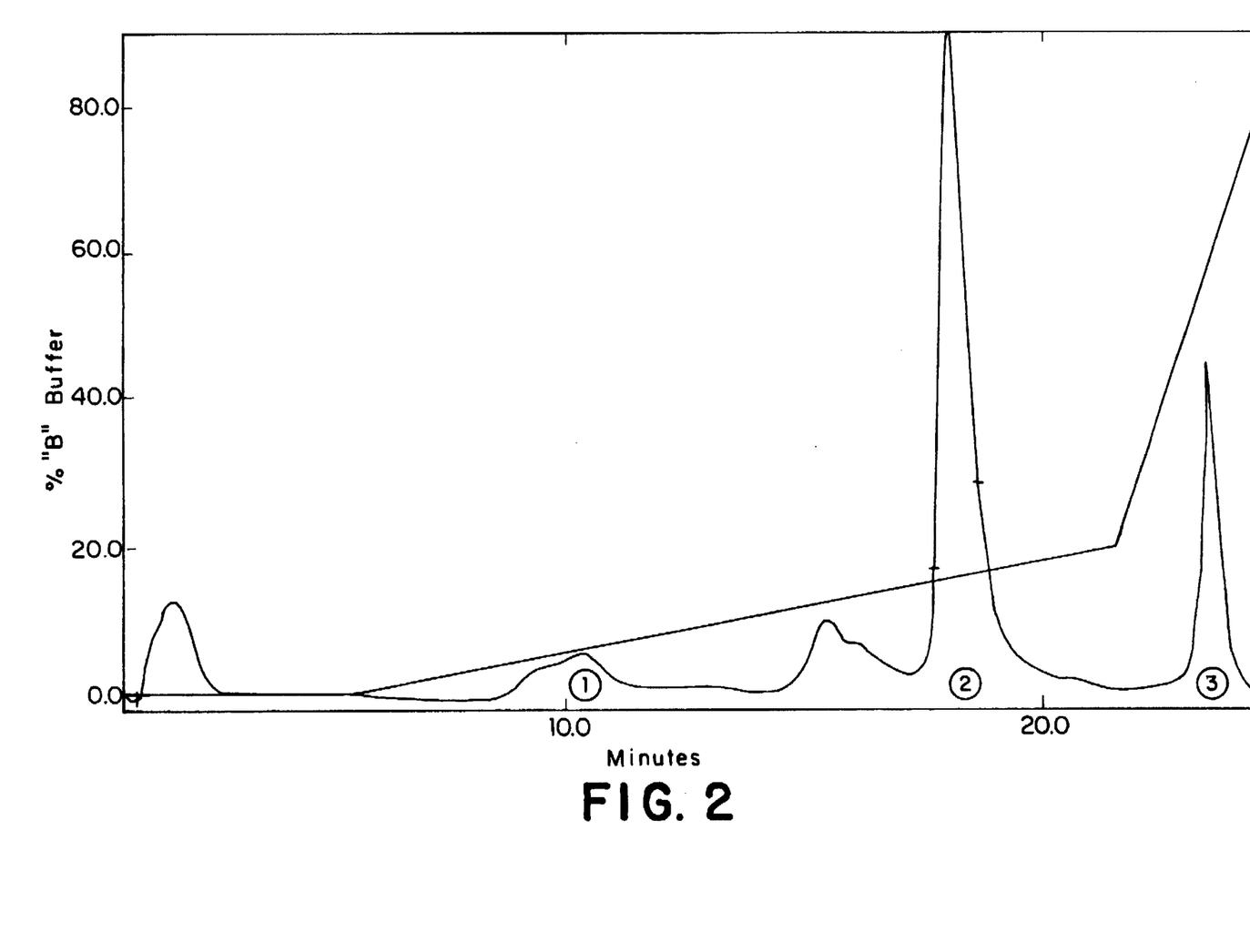
FIG. 2 depicts a chromatogram representing the separation of fraction 2 (from FIG. 1) by anion exchange chromatography on a Mono-Q column.
Figure 3:
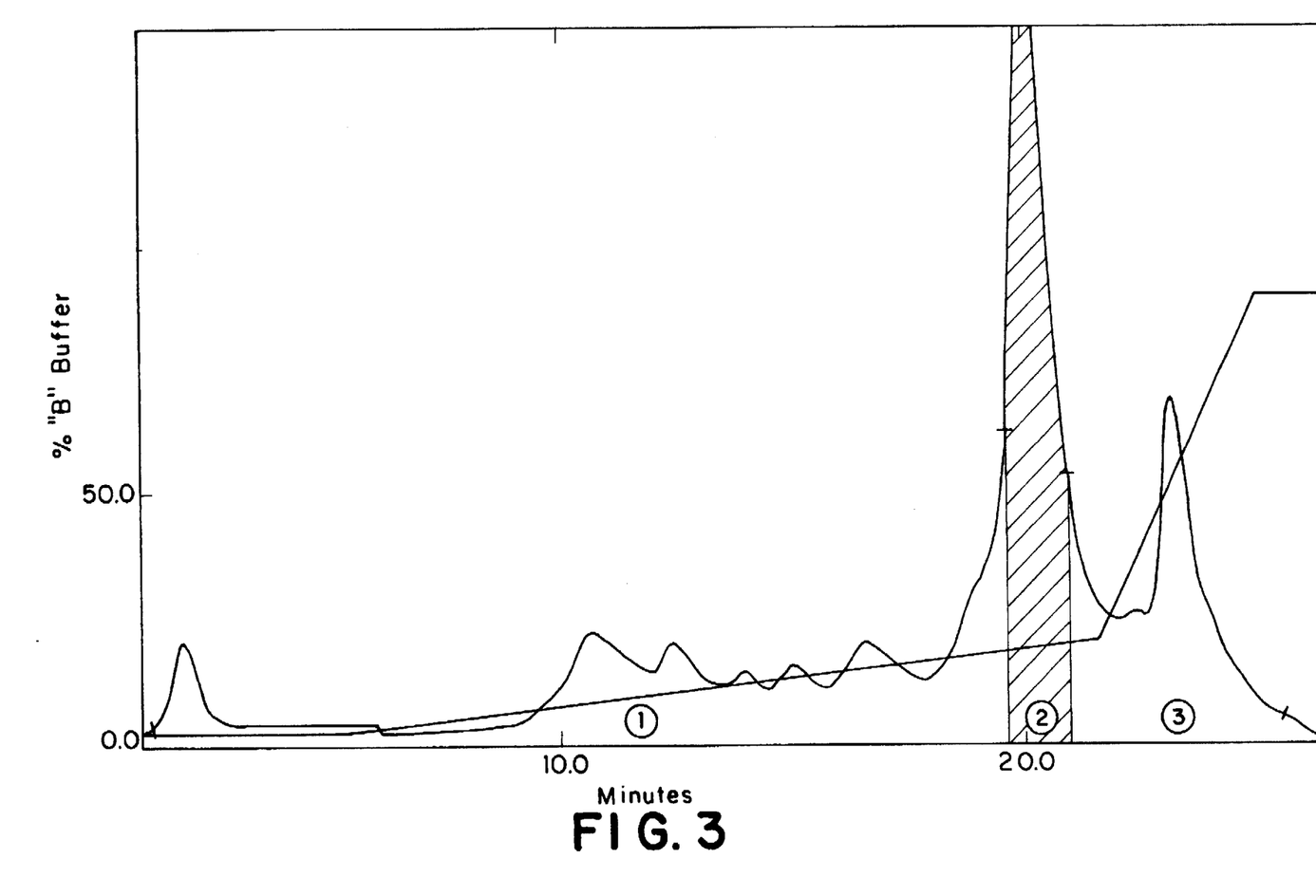
FIG. 3 depicts a chromatogram representing the separation of fraction 5 (from FIG. 1) by anion exchange chromatography on a Mono-Q column.
Figure 4A:
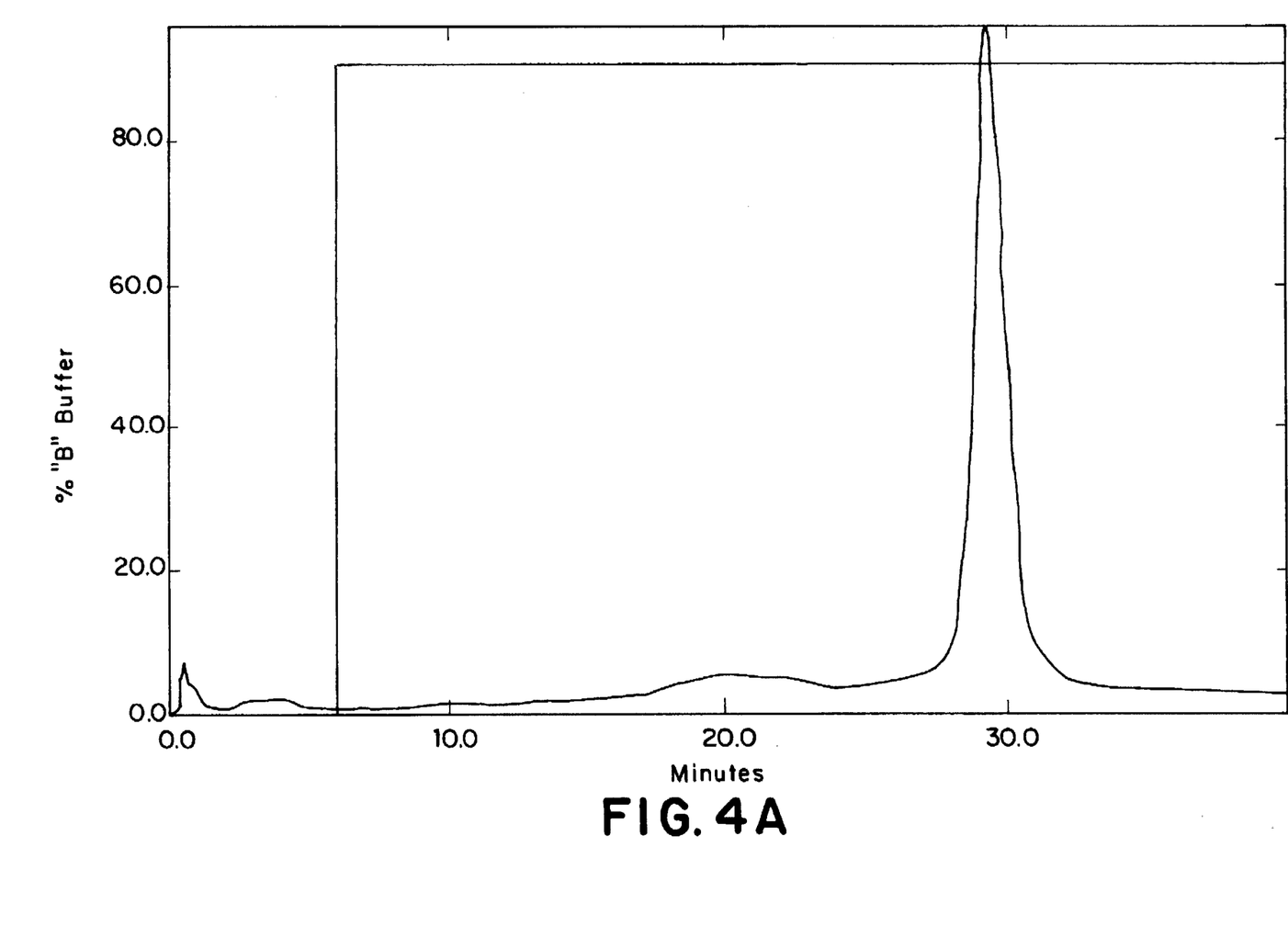
FIGS. 4A and 4B depict chromatograms representing the separation of fractions 2 (FIG. 4B) and 5 (FIG. 4B) (obtained from FIGS. 2 and 3, respectively) by chromatofocusing on a Mono-P column.
Figure 4B:
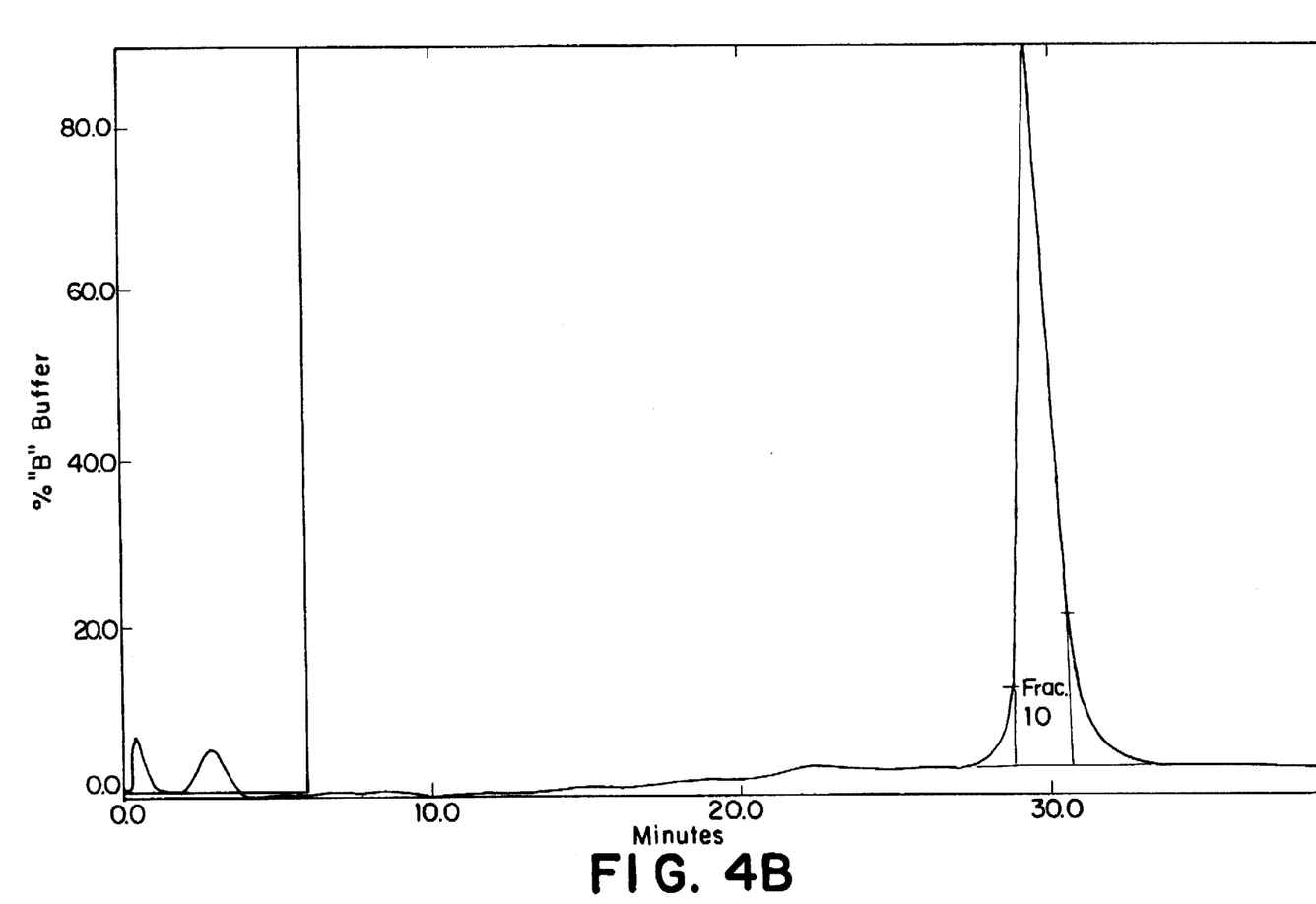

Approximately 75 μl of fraction 2 from AEC of IMAC fraction 2,depicted in FIG. 2, and 75 μl of fraction 2 from AEC of IMAC fraction 5,depicted in FIG. 3, was diluted to 1.0 ml with buffer A. Chromatofocusing was performed using a Mono-P column (5.0×50 mm). The A buffer was 25 mM Bis-Tris adjusted to pH 7.2 and the B buffer was a 1:10 dilution of Polybuffer 74 adjusted to pH 5.0. The column was eluted at a flow rate of 0.5 ml/min with 0% B buffer for 5 min then immediately switching to 100% B. This chromatography was monitored at 280 nm and fractions collected with a Gilson model 203 fraction collector. The resultant chromatograms are shown in FIGS. 4A and 4B. The chromatofocusing product of AEC fraction 2 of IMAC fraction 5 was injected into TBW larvae as described previously. The larvae were analyzed initially and after 24 and 48 hours for paralysis and feeding inhibition and the results are indicated in Table V. As indicated in Table V, the chromatofucusing fraction contained paralytic and feeding inhibitory activity for TBW larvae. The chromatofocusing product of AEC fraction 2 of IMAC fraction 2 is referred to as BW2. The chromatofocusing product of AEC 2 of IMAC fraction 5 is referred to as BW5. The N-terminal sequence of both proteins is: Asp-Gly-Ile-Val-Gly-Lys-Ala-Ser-Ser-Tyr-Ala-Ala-Leu (SEQ ID NO:1).

TABLE V

Chromatofocusing of AEC Fraction of IMAC Fraction of C-100 Retentate of *Phidippus audax* Whole Venom Contains Paralytic and Feeding Inhibitory Activity in TBW Larvae

| Sample | Dose[a] | Initial | 24 hours[b] | 48 hours[b] |
|---|---|---|---|---|
| Control (PBS) | — | 0/6 | 0/6 | 0/6 |
| Cu5/MQ2/MP1 | 21.3 | 3/3 | 0/3[c] | 1/3[c] |
| Cu5/MQ2/MP1 | 40.5 | 2/2 | 1/2[c] | 1/2[c] |

[a]This value represents the dosage of the fraction injected in terms of μg of protein per g of larvae.
[b]This value represents the number of larvae paralyzed versus total number of larvae injected.
[c]All of these larvae exhibited complete feeding inhibition at 24 and 48 hours.

Example 6

Isolating The Coding Genes for Insecticidally Effective Peptides Isolated from *Phidippus audax* Venom Step #1: RNA Isolation Spiders are collected from known wild populations and identified as *Phidippus audax*. Live spiders are frozen and the cephalothorax removed under liquid nitrogen. RNA is extracted from the cephalothoraxes using the protocol of Chomczynski, et al., *Analytical Biochemistry*, 1987, 162, 156. Polyadenylated messenger RNA (mRNA) is purified using oligo d(T) cellulose (Pharmacia LKB, Sweden) chromatography.

Step #2: cDNA Synthesis

Messenger RNA is reverse transcribed to cDNA with murine leukemia virus reverse transcriptase (Bethesda Research Laboratories, Md.) using the manufacturer's protocol. The 20 μl reaction mixture contains the enzyme buffer as supplied in a cDNA synthesis kit (Boehringer Mannheim, Ind.), 50 ng of mRNA, 2 units of RNase H, 30 ng of d(T)Not I primer (Promega, Madison, Wis.), 1 mM each deoxynucleoside triphosphates, and 100 μg of reverse transcriptase. The reaction mixture is incubated for 1 h at 37° C. and continued for 10 minutes at 42° C. The reaction mixture is ethanol precipitated and resuspended in 20 μl water.

Step #3: Primer Synthesis

A degenerate primer DNA sequence mixture which could code for amino acid residues 1 through 8 is designed using codon preferences to reduce degeneracy.

Step #4: Amplification

Primer directed enzymatic amplification of DNA with a thermostable DNA polymerase was initially described by Saikki, et al., *Science*, 1988, 239, 487. For this application, 5 μl of the Phidippus cephalothorax cDNA is used as template in a polymerase chain reaction containing reagents contained in the GENEAMP™ DNA amplification kit (Perkin Elmer Cetus, Calif.). The amplification reaction contains the sense and antisense primers in a 2 μM concentration, 100 μM of each deoxynucleotide triphosphate, and 4 units of the thermostable recombinant TaqI polymerase. The reaction is run in a DNA Thermal Cycler manufactured by Perkin Elmer Cetus using both high and low stringency reactions.

Step #5: Cloning of PCR Products

The PCR products from both high and low stringency reactions are purified to remove unincorporated primers using a Centricon-100 (Amicon) molecular size separation unit. The retained products are then digested with the restriction enzyme Not I (MBR), Milwaukee, Wis.), which cleaves within the downstream (3' end) primer leaving a sticky end. The vector, pKS (Stratagene, Lajolla, Calif.), is double digested with EcoRV (US Biochemical) and Not I to generate sites specific for directional cloning. Vector and insert are ligated and transformed into complex DH5αF'. Colony lifts are screened with the $^{32}$p labeled internal probe and candidate colonies are further characterized by sequencing (US Biochemical's Sequenase Version 2.0) mini-prep DNA using the internal probe as primer.

Example 7
Recombinant Baculovirus Construction

A lepidopteran signal sequence (Jones, et al., *J. Biol. Chem.*, 1990, 265, 8596), is constructed from two synthetic oligonucleotides using the method of Rossi, et al ., *J. Biol. Chem.*, 1982, 257, 9226. Two 48 mers are purified by ion exchange chromatography. These two oligonucleotides share eleven base pairs of complementary sequence at their 3' termini. When the sequences are annealed in the presence of the four deoxy-ribonucleoside triphosphates and the Klenow fragment of DNA polymerase I, a double-stranded product is synthesized. Reaction products are purified using hydroxylapatite chromatography and the double-stranded DNA molecules are digested with AatII, the restriction enzymes appropriate for inserting this sequence upstream of cDNA cloned into pKS-DK9c. Subclones are screened for the insertion of the signal sequence and evaluated by DNA sequencing.

DNA sequencing confirms an in-frame fusion between the two cDNA sequences. The entire synthetic gene construct is excised and adapted for cloning into the NheI site of pBlueBac, a baculovirus transfer vector (Vialard, et al., *J. Virology*, 1990, 64, 3–50). Subclones are sequenced to confirm the correct insertion of the construct. DNA sequencing of plasmid WR9 confirms the insertion of the synthesized gene in the baculovirus transfer vector pBlueBac. The use of the pBlueBac vector expedites the screening process as insertion of the recombinant gene into the baculovirus genome is accompanied by co-expression of β-galactosidase and detectable by a color change when grown on indicating media.

Recombinant baculoviruses are produced by transfection of *Spodoptera frugiperda* strain Sf9 (ATCC# CRL1711) cells with a mixture of 1 μg AcMNPV viral DNA and 2 μg plasmid DNA using the protocol of Summers and Smith (in "A Manual of Methods for Baculovirus Vectors and Insect Cell Culture Procedures", Texas Agricultural Experiment Bulletin No. 1555, 1988). Four days post-transfection, dilutions of the cell supernatant are plaqued on 100 mm plates seeded with $5 \times 10^6$ Sf9 cells and covered with agarose containing Bluo-gal (Gibco BRL, Gaithersburg, Md.) as substrate. Within 5 to 6 days, recombinants are detectable by their pale blue color. Plaques are picked using a pasteur pipet and eluted in 1 ml of media. This eluent is used to re-infect Sf9 cells seeded into a T-25 flask. Three days post-infection a small volume of supernatant is collected from six different isolates and used to prepare viral DNA. PCR amplification using viral specific primers from the region surrounding the polyhedrin gene confirms that viral isolates contain an appropriately sized insert and lacked any wild-type contamination. Titered stocks of the recombinant viruses are then prepared for in vivo and in vitro testing.

MAMMALIAN TOXICOLOGY

Whole venom and the C-100 retentate fraction of whole venom were tested at doses of 5 and 10 WVE/mouse, respectively, in male Swiss-Webster mice (25–30 g) by intraperitoneal (i.p.) injection (n=1). Samples were diluted in physiological saline prior to injection; control mice were injected with equivalent volumes of saline. Mice were observed continuously for the first several hours after treatment, and then periodically for 48 hours. The only visible effect of the C-100 retentate fraction was a slight twitching of the subcutaneous muscles. This slowly subsided over several hours; no other effects were noted at any time. No effects were noted from the saline injection or the whole venom injection.

---

---

What is claimed:

1. A substantially purified, insecticidally effective protein from Phidippus spider venom characterized as causing flaccid paralysis when injected into larvae of at least one member of the class Insecta, wherein said protein comprises an N-terminal amino acid sequence having SEQ ID NO:1.

2. The protein of claim 1 wherein the spider venom is from *Phidippus audax*.

3. An insecticidal composition comprising an insecticidally effective amount of a substantially purified, protein from Phidippus spider venom, characterized by causing flaccid paralysis when injected into larvae of at least one member of the class Insecta, in an agriculturally or horticulturally acceptable carrier, wherein said protein comprises an N-terminal amino acid sequence having SEQ ID NO:1.

* * * * *